United States Patent [19]

Sugerman

[11] Patent Number: 5,314,930
[45] Date of Patent: May 24, 1994

[54] BETA KETO MIXED ACYLATE MONOMERS

[76] Inventor: Gerald Sugerman, 8 Cambridge Dr., Allendale, N.J. 07401

[21] Appl. No.: 42,534

[22] Filed: Apr. 5, 1993

[51] Int. Cl.$^5$ .................. C07C 69/52; C08G 2/22; C08G 2/26; C08G 2/16
[52] U.S. Cl. .................. 522/34; 522/182; 522/904; 523/160; 523/400; 528/220; 554/224; 560/224
[58] Field of Search .......... 522/34, 904, 182; 554/224; 528/220; 523/400, 160; 560/224

[56] References Cited

U.S. PATENT DOCUMENTS

| | | | |
|---|---|---|---|
| 2,666,701 | 1/1954 | West | 522/904 |
| 4,093,577 | 6/1978 | Konno et al. | 522/904 |
| 4,144,157 | 3/1979 | Guse et al. | 522/904 |
| 4,424,325 | 1/1984 | Tsunoda et al. | 522/904 |
| 4,977,293 | 12/1990 | Hatton et al. | 522/904 |
| 5,064,892 | 11/1991 | Hofland et al. | 554/224 |
| 5,248,805 | 9/1993 | Boettcher et al. | 522/904 |

*Primary Examiner*—Susan Berman
*Attorney, Agent, or Firm*—Roger L. Fidler

[57] ABSTRACT

Novel ketone monomers containing both alpha-beta unsaturated acylate and unsaturated fatty acylate substituents on more carbon atoms beta to the carbonyl group (Formula 1) have been found to be surprisingly useful in a variety of essentially pollution free coatings applications.

$$a,b,cCC(O)Cd,e,f \qquad \text{Formula I}$$

Wherein not less than one, but no more than three of a,b,d and e are each independently chosen from among monovalent ligands having the structure $-CH_2O_2CCR=CR'R''$ (wherein each of R,R', and R'' is independently chosen from among hydrogen, methyl or ethyl ligands); and wherein at least one, but not more than three of a,b,d and e are each independently chosen from among monovalent ligands having the structure: $-CH_2O_2CC_nH_{2(n-x)+1}$ (wherein n is an integer from one to thirty; x is an integer from 0 to 4, but less than $[n/2-1]$); and wherein both the nonacylate members of the group a,b,d, and e, as well as c and f, are each independently chosen from among hydrogen, or monovalent one to 12 carbon hydrocarbyl ligands. Optionally two or more of said hydrocarbyl ligands may be conjoined to form ring structures.

12 Claims, No Drawings

BETA KETO MIXED ACYLATE MONOMERS

BACKGROUND OF THE INVENTION

Affordable, essentially pollution free coatings have been the "holy grail" of the various subsets of the coatings art since the onset of environmental concerns. Prior art which attempted to achieve this end almost invariably employed one or more impractical requirements. These included massive capital investment, highly toxic/expensive materials, and/or substantial energy consumption. The instant invention eliminates these impediments by employing low toxicity, modest cost materials, in existing facilities, at greater energy efficiencies than the toxic formulations replaced while simultaneously upgrading product performance.

BRIEF DESCRIPTION OF THE INVENTION

The subject invention relates to the preparation and application of low toxicity, moderate cost reactive diluents, which when properly formulated into conventionally employed coatings permit the virtual elimination of both volatile organic compounds (VOCs) and toxic heavy metal requirements, while providing performance and processing properties equal to, or superior, in every meaningful respect, to those of the best conventionally formulated analogs.

In one embodiment of the invention, the above stated performance objective has been achieved via the synthesis and evaluation of the new and novel beta keto mixed acylate monomers of the instant invention (cf Formula I), and their employment in appropriate formulations as reactive diluents.

Via the employment of the new and novel mixed beta keto acylate monomers of the instant invention (partly as replacements for the solvents conventionally employed) dramatic improvements in performance and simultaneous quantum leaps in pollution control have been demonstrated.

DETAILED DESCRIPTION OF THE INVENTION

Novel ketone monomers containing both alpha-beta unsaturated acylate and unsaturated fatty acylate substituents one or more carbon atoms beta to the carbonyl group (Formula 1) have been found to be surprisingly useful in a variety of essentially pollution free coatings applications.

$$a,b,cCC(0)CD,e,f \quad \text{Formula I:}$$

Wherein not less than one, but no more than three of a,b,d and e are each independently chosen from among monovalent ligands having the structure $-CH_2O_2CCR=CR'R''$ (wherein each of R, R', and R'' is independently chosen from among hydrogen, methyl or ethyl ligands) and wherein at least one, but not more than three of a,b,d and e are each independently chosen from among monovalent ligands having the structure: $-CH_2O_2CC_nH_{2(n-x)+1}$ (wherein n is an integer from one to thirty; x is an integer from 0 to 4, but less than $[n/2-1]$); and wherein both the nonacylate members of the group a,b,d, and e, as well as c and f, are each independently chosen from among hydrogen, or monovalent one to 12 carbon hydrocarbyl ligands. Optionally two or more of said hydrocarbyl ligands may be conjoined to form ring structures.

Table 1 provides a small sampling of specific examples of the new and novel beta keto mixed acylates, and Table II provides a number of generic examples of their beneficial application. Both tables and the appended examples (1 through 7) are intended to be illustrative of, rather than exhaustive of the utility and/or the scope of this invention. Those skilled in the art will readily observe that the benefits of this invention may survive noncritical molecular modification(s) of Formula I, e.g. the inclusion of sulfonyl, acetal, ether and/or orthoester groups as appendages on the various "R: ligands, without departing from the spirit of this invention. In general, efficacy in the employment of the new and novel beta keto mixed acylates of the instant invention in coatings applications, requires application usages in excess of about three weight percent of the liquid portion of the formulation, however in some instances proportions as low as one percent, have surprisingly been found to confer substantial benefits, e.g. enhanced leveling, wetting, and pinhole reduction, particularly on metallic substrates. It has been found that in coatings related applications that aliphatic ketone derived products of the instant invention tend to outperform their aromatic analogs in ambient cure systems, and that the reverse is generally true of thermally and radiation cured coatings. Table (A) which illustrates species of the type(s) of mixed beta keto mixed esters, Table (B) which defines some of their coatings applications, and Examples (1) through (7) which follow, are intended to illustrate rather than to delimit either the scope of the nature or the range of the utility of the instant invention.

TALBE A

Examples of the beta keto mixed acylate monomers of the instant invention.

| | a | b | c | d | e | f |
|---|---|---|---|---|---|---|
| A) | $-CH_2O_2CCH=CH_2$ | $CH_2O_2C=CH_2$ | H | $CH_2O_2CC_{17}H_{29}$ | $CH_2O_2CCH=CH_2$ | H |
| B) | $-CH_2O_2CCCH_3=CH_2$ | H | $C_2H_2CH_3$ | $CH_2O_2CC_{12}H_{25}$ | $CH_3$ | H |
| C) | $-CH_2O_2CCH=CH_2$ | $CH_2O_2CCH=C_2H_5$ | H | $CH_2O_2CC_{17}H_{31}$ | $C_6H_5$ | H |
| D) | $-CH_2O_2CCH=CH_2$ | $CH_2O_2CCH=CH_2$ | H | $CH_2O_2CC_8H_{17}$ | $CH_2O_2CCH=CH_2$ | H |
| E) | $-CH_2O_2CCCH_3=CH_2$ | $CH_3$ | H | $CH_2O_2CC_{17}H_{33}$-iso | $CH_2O_2CCH=CH_2$ | $CH_3$ |
| F) | $-CH_2O_2CCH=CH_2$ | $(CH_2)$ | — | $CH_2O_2CC_6H_{10}$ | $(CH_2)_2$ | H |
| G) | $-CH_2O_2CCCH_3=CH_2$ | $CH_2O_2CCH=CH_2$ | $CH_3$ | $CH_2O_2CC_{13}H_{23}$ | $CH_3$ | H |
| H) | $-CH_2O_2CCH=CH_2$ | $CH_2O_2CCH=CH_2$ | $CH_3$ | $CH_2O_2CC_{17}H_{29}$ | $CH_3$ | H |
| J) | $-CH_2O_2CCCH_3=CH_2$ | H | H | $CH_2O_2CC_{24}H_{43}$ | $CH_3$ | $CH_3$ |
| K) | $-CH_2O_2CCH=CH_2$ | H | H | $CH_2O_2CCH_3$ | H | H |

TABLE B

Examples of coating types benefitted by inclusion of the compounds of the instant invention.

| | |
|---|---|
| adhesive | anticorrosive |
| chemically cured | decorative |
| inks | radiation cured |
| thermally cured | |

EXAMPLES

Example (1)

This example teaches the preparation of the beta keto mixed acylate monomers of the instant invention from the corresponding methylol ketones.

One mole of 1,1,2,2- tetramethylol acetone (178 g), 3 moles of acylic acid, (216 g), 100 g of cyclohexane (azeotropic agent), 0.5 g each of hydroquinone and benzoquinone (polymerization inhibitors), together with 2.0 g of methanesulfonic acid were refluxed with continuous decantation of condensate water, for a period of five hours. During said period, 2.88° ° moles (51.8 g) of water was separated from the reflux condensate. One mole (278 g) of linolenic acid was then added, and the reflux/decantation continued for an additional six hours, after which a further 1.01 (18.2 g) of water was collected. Product was neutralized with aluminum hydroxide to pH 6.5, washed five times with 200 cc of 5% aqueous potassium bicarbonate, and devolatilized in vacuo, to produce 568 g of a bottoms product bp$_{10}$>150° C. High pressure liquid chromatography indicated a major component purity of 94%; hence an overall yield of 89%. Calculated for (A) ($C_{34}H_{48}O_9$): C, 68.00; H, 8.00. Found: C, 67.79; H, 8.03.

Similarly prepared on a comparable scale, from the indicated feedstocks via similar technology, and with the stated yields and analytical values were compounds (B) through (F) respectively, cf. Table 1.

TABLE 1

Beta Keto Mixed Acylates From Methylol Ketones

| Compd. | Methylol ketone | 2,3-unsat. acid/M | catalyst g | fatty acid/ M | yield % | Calc C/H Found C/H |
|---|---|---|---|---|---|---|
| B | B' | M/1 | TiPT 2 | TD 1 | 72 | 64.71/11.27 64.92/11.41 |
| C | C' | A/1 | MSA | lio-leic | 67 | 71.92/8.90 |
|   |    | 2-butenoic/1 | 1 | 1 |   | 72.04/8.79 |
| D | D' | A/3 | 4-DMAP 3 | N 1 | 63* | 59.46/8.11 59.67/8.32 |
| E | E' | M/1 | MPP 2.5 | i-O 1 | 64* | 67.70/10.55 68.01/10.57 |
| F | F' | A/1 | MSA 2 | Hp | 73 | 63.38/8.57 63.11/8.48 |

Example (2)

This example teaches the preparation of the beta keto mixed acylate monomers of the instant invention from the corresponding ketones.

A solution of one mole of 2-propiophenone (134 g) in 250 ml of n-pentane containing 3 g of 4-DMAP and one mole of linoleic acid (280 g) was sparged with one mole (60 g) of 50% formalin over a period of two hours with continuous decantation of azeotroped water. Water recovery was 46.2g (96% of theory). Two moles of acrylic acid were added and an additional 120 g of 50% formalin sparged over a three hour period at reflux with continuous water decantation. Total water recovery 135.8 g (94%) this was followed by washing with five 250 ml portions of 5% potassium bicarbonate solution and devolatization to produce a bottoms product in 571 g (98%) yield; virtually identical to (C) by infrared spectroscopy.

Similarly prepared from appropriate ketones were analogous beta keto mixed acylates, cf Table 2

TABLE 2

Direct Preparation of beta keto Mixed Acylates from Ketones

| Compd. | ketone | 2,3-unsat. acid/M | catalyst g | fatty acid/ M | yield % | Calc C/H Found C/H |
|---|---|---|---|---|---|---|
| F | cyclhexanone | M/1 | TEA 3 | Hp/1 | 86 | 63.38/8.57 63.14/8.69 |
| G | 2-pentanone | M/1 | 4-DMAP 2 | TDD/1 | 71 | 68.38/9.57 68.09/9.43 |
| H | 2-pentanone | A/2 | TEA 2 | Li/1 | 62 | 68.50/9.65 68.78/9.39 |
| I J | 2-methyl-3-butanone | M/1 | TEA 3 | PC/1 | 74 | 73.88/9.33 |
| K | acetone | A/1 | TEA 2 | acetic acid | 81 | 56.07/6.54 55.89/6.71 |
| L | o-MP | S/1 | TFA 3 | Li/2 | 65* | 84.16/10.58 83.89/10.27 |

Notes:
B' = 2,4-dimethylol-5-heptanone
C' = 1,3,3-trimethylol-2-propiophenone
D' = 1,1,3,3-tetramethylol acetone
E' = 1,1,3-trimethylol-2-pentanone
F' = 2,6-dimethylol cyclohexane
A = acrylic acid
DMAP = 4-dimethylamino pyridine
Hp = heptenoic acid
i-O = iso oleic acid
M = methacrylic acid
MPP = methanesulfonyl diphosphate
MSA = methane sulfonic acid
N = n- nonanoic acid
o-MP = ortho methoxy propiophenone
PC = pentaeicosanedienoic acid
S = sorbic acid
TD = n-tridecanoic acid
TDD = n-tetradecadienoic acid
TEA = triethylene diamine
TFA = trifluoroacetic acid
TiPT = tetraisopropyl titanate
* = isomer resolution incomplete

Example (3)

This example teaches the utility of the products of the instant invention as essentially VOC (volatile organic compound) free reactive diluents in peroxide cured, e.g. thermoset polyester coatings.

A 60 wt % solution of polybutylene maleate ($M_n$ 2650, $M_w$ 5890) in 40 wt % of the indicated diluent was thoroughly admixed with an equal weight of 0.9 micron aluminum trihydrate and 0.7 wt % of benzoyl peroxide, and the resulting dispersion cast at ambient then cured for two hours at 90° C. The cured casting was annealed at 25° C. for 24 hours and selected properties evaluated. Data thus generated are reported in Table 3.

TABLE 3

Evaluation of beta keto mixed acylates vs. conventional (reactive) poly ester diluents

| Diluent | Dispersion visc. kcps | tear str. pa/cm | adhesion to cs[1] kpa | Weight loss % |
|---|---|---|---|---|
| styrene | 769 | 12 | 37 | 17 |
| vinyl toluene | 910 | 16 | 41 | 9.5 |
| divinyl benzene | 1471 | 25 | 53 | 2.1 |
| A | 1385 | 38 | 61 | >0.1 |
| B | 843 | 32 | 65 | >0.1 |
| C | 890 | 24 | 68 | >0.1 |
| F | 687 | 43 | 58 | >0.1 |
| H | 1125 | 31 | 62 | >0.1 |
| J | 972 | 29 | 48 | >0.1 |
| K | 592 | 37 | 60 | 0.2 |

Note 1, carbon steel.

This example clearly demonstrates that the products of the instant invention not only provide superior polyester film properties, and reduced volatilization (with consequent minimized shrinkage) as compared to their conventional polyester diluent counterparts, but surprisingly low (uncured) dispersion viscosities as an additional benefit.

Example (4)

This example teaches the utility of the products of the instant invention in ink formulations, e.g. sheetfed lithographic ink.

Sheetfed inks were prepared by dispersing 18 wt % of N550 carbon black and 3 wt % of alkali blue in a varnish comprised of 30 wt % of rosin ester in linseed oil, containing 150 ppm each of cobalt and manganese dryer(s) and extended with 12 wt % of the indicated diluent. The resulting inks were printed on 30 lb coated stock and dry times and appearance observed. Results are tabulated in Table 4.

TABLE 4

Evaluation of beta keto mixed acylates in Sheetfed inks.

| Diluent | Dry time min. | 60° gloss % | Dot gain % |
|---|---|---|---|
| naphthenic oil b.p. 315° C. | 53 | 67 | 18 |
| A | 29 | 76 | 3 |
| D | 45 | 71 | 2 |
| E | 21 | 70 | 4 |
| F | 34 | 77 | 1 |

From the foregoing it is obvious the beta keto mixed acylates of the instant invention provide substantial benefits when substituted naphthenic oil in sheetfed inks.

Example (5)

This example teaches the utility of the products of the instant invention in radiation cured coatings, e.g. wood coatings.

Ultraviolet cured clear wood coatings were prepared by dissolving 5 wt % each of benzil and carnauba wax in a vehicle containing 70 wt % vinyl ester acrylate (Mn 3,400, Mw 12,365), and 20 wt % of the indicated diluent. The coatings were applied to white pine at 1 mil by direct roll coating, cured by exposure to mercury arc lamps and the finished films evaluated for (Tabor) rub, and water resistance and gloss. The data are detailed in Table 5.

TABLE 5

Performance of beta keto mixed acylates in wood coatings

| Diluent | Rub resistance cycles | Water resistance hr. 60° C. | 60° gloss % |
|---|---|---|---|
| TMPTA | 120 | 5.6 | 79 |
| TMPTA* no cure | | | |
| PETA | 159 | 4.8 | 80 |
| PETA* no cure | | | |
| TEGDA | 91 | 5.9 | 74 |
| A | 164 | 7.9 | 76 |
| C | 203 | 9.7 | 84 |
| C* | 253 | 11.4 | 86 |
| H | 181 | 10.2 | 80 |
| H* | 201 | 9.4 | 87* |

Notes:
*Photoinitiator omitted
TMPTA: trimethylol propane triacrylate
PETA: pentaerythritol tetraacrylate
TEGA: triethylene glycol diacrylate The preceding demonstrate that the products of the instant invention outperform the conventionally employed diluents in UV coatings even when the expensive, highly toxic and extractable photoinitiator(s) are eliminated from (only) their formulations.

Example (6)

This example teaches the utility of the products of the instant invention in thermally cured coatings, e.g. anticorrosive coil coatings.

Five weight % of the indicated reactive diluent was dispersed in a 42% solids acrylic latex (methyl acrylate, butyl acrylate copolymer) containing 7 weight % butyl cellosolve coalescent, and 8% of methoxy melamine curative. The resulting dispersion was applied at 2.5 mils wet to cold rolled steel, followed by a 25 minute bake at 160° C. The baked coated panels were subjected to saturated salt spray at 75° C. for 1000 hours and the films evaluated, the results are tabulated in Table 6.

TABLE 6

Evaluation of the beta keto mixed acylates of the instant invention as anticorrosives in coil coatings.

| Diluent | Post Salt Spray Film appearance | Corrosion rate mils/year |
|---|---|---|
| none | fully delaminated | >200 |
| TMPTA | fully delaminated | 87 |
| HDDA | fully delaminated | 71 |
| C | adherent | 29 |
| D | adherent | 21 |
| D* | adherent | 32 |
| E | partly adherent | 57 |
| G | adherent | 17 |

Note
*1% diluent addition level

The film adhesion and anticorrosion benefits consequent to the employment of the products of the instant invention in melamine cured latex acrylic films as compared to either control or prior art analogs are obvious from the data in Table 6.

Example (7)

This example teaches the utility of the products of the instant invention in hot melt adhesive coatings, e.g. melamine urea.

A series of epoxy powder coatings based hot melt adhesives were prepared by intensive blending of 73 parts by weight (pbw) of 2000 mw solid bis phenol A type epoxy oligomer, 7 pbw of micronized urea, 15 pbw of delaminated, 400 mesh calcined clay, and 5 pbw of the indicated diluent. The resulting mix was doctor blade applied to copper sheet at 2 mils, and laminated to a second sheet at 15 psi for 2 minutes at 170° C. After which the laminates were cooled to 25° C. over about 4 hours, then tested for peel strength. Results are reported in Table 7.

TABLE 7

Evaluation of beta keto mixed acylates in a hot melt adhesive.

| Diluent | Peel strength Kpa |
|---|---|
| none | 162 |
| PETA | 169 |
| melamine | 165 |
| C | 187 |
| K | 174 |
| J | 182 |

The enhanced adhesion consequent to the employment of the products of the instant invention in epoxy urea appears to be provided in part by improved adhesive flowout, a phenomenon easily observed, but difficult to quantify, with these additives in the above system.

I claim:

1. A composition of matter comprising the class of beta keto mixed acylate monomers containing both one to three alpha-beta unsaturated carboxylate groups, and at least one other type of carboxyl derived substituent group on one or more carbon atoms beta to the carbonyl group, and which conforms to the composition described in Formula 1:

$$a,b,cCC(O)Cd,e,f \qquad \text{Formula I}$$

wherein not less than one but no more than three of a,b,d and e are each independently chosen from among monovalent ligands having the structure $-CH_2O_2CCR=CR'R''$ (wherein each of R,R', and R'' is independently chosen from among hydrogen, methyl or ethyl ligands); and wherein at least one, but not more than three of a,b,d and e are each independently chosen from among monovalent ligands having the structure: $-CH_2O_2CC_nH_{2(n-x)+1}$ (wherein n is an integer from one to thirty; x is an integer from 0 to 4, but less than $[n/2-1]$); and wherein both the non acylate members of the group a,b,d, and e, as well as c and f are each independently chosen from among hydrogen, or monovalent one to 12 carbon hydrocarbyl ligands. Optionally two or more of said hydrocarbyl ligands may be conjoined to form ring structures.

2. The composition of matter of claim 1 wherein n is at least 5 but less than 30.

3. The composition of matter of claim 1 wherein at least two of a,b,d and e are each independently chosen from among monovalent ligands having the structure $-CH_2O_2CCR=CR'R''$ (wherein each of R,R', and R'' is independently chosen from among hydrogen, methyl or ethyl ligands).

4. The composition of matter of claim 1 wherein a,b and d are each methyleneacrylate, methylenemethacrylate ligands or a combination of such ligands.

5. The composition of matter of claim 1 wherein a,b and d are each methyleneacrylate, methylenemethacrylare ligands or a combination of such ligands, and c and f are each hydrogen and e is a methylene ester of a six to thirty carbon fatty acid.

6. The composition of matter of claim 1 wherein a and d are each methyleneacrylate, methylenemethacrylate ligands or a combination of such ligands, b and d are each hydrogen, and e and f are collectively $n-C_3H_6$.

7. A coating formulation in which a composition of matter as in claim 1 is employed at a concentration of from one percent (1%) to about fifty percent (50%) by weight.

8. A coating formulation in which a composition of matter as in claim 1 is employed at a level of from one percent (1%) to about fifty percent (50%) by weight in a thermoset polyester.

9. A coating formulation in which a composition of matter as in claim 1 is employed at a level of from one percent (1%) to about fifty percent (50%) by weight in an ink.

10. A coating formulation in which a composition of matter as in claim 1 is employed at a level of from one percent (1%) to about fifty percent (50%) by weight in a radiation cured coating.

11. A coating formulation in which a composition of matter as in claim 1 is employed at a level of from one percent (1%) to about fifty percent (50%) by weight in a thermally cured coating.

12. A coating formulation in which a composition of matter as in claim 1 is employed at a level of from one percent (1%) to about fifty percent (50%) by weight in a hot melt adhesive coating.

* * * * *